United States Patent
Yamashita et al.

(10) Patent No.: US 6,462,233 B1
(45) Date of Patent: Oct. 8, 2002

(54) PROCESS FOR THE PREPARATION OF SORBIC ACID

(75) Inventors: Akira Yamashita; Mitsuhiro Kouno, both of Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/555,294

(22) PCT Filed: Sep. 21, 1999

(86) PCT No.: PCT/JP99/05126

§ 371 (c)(1),
(2), (4) Date: May 26, 2000

(87) PCT Pub. No.: WO00/20367

PCT Pub. Date: Apr. 13, 2000

(30) Foreign Application Priority Data

Oct. 5, 1998 (JP) .......................................... 10-282250

(51) Int. Cl.$^7$ .............................................. C07C 57/10
(52) U.S. Cl. ...................................................... 562/601
(58) Field of Search ........................................ 562/601

(56) References Cited

U.S. PATENT DOCUMENTS 3,696,147 A * 10/1972 Kunstle et al.
3,997,598 A   12/1976 Fernholz et al.

FOREIGN PATENT DOCUMENTS

| JP | 4426646 | 11/1969 |
| JP | A-54103821 | 8/1979 |

OTHER PUBLICATIONS

Derwent abstract of DE 3143091 A. Neu et al. (1983). Prodn of pure sorbic acid—by recrystallization from water under pressure.*

Derwent abstract of DE 2103051. Sorbic acid purifcn and stabilisation—using prior crystallization mother liquor (1975).*

Derwent abstract of JP 69026646 B. Sorbic acid prepd by decomposition of the polyester (1968).*

CAPLUS abstract 1967:37378. Polyanskii et al. (1967). Synthesis of sorbic acid from ketene and crotonaldehyde. Zh. Prikl. Khim. 39(10): 2314–9.*

Derwent abstract of JP 54103821 A. Ogawara et al. (1979). Method of recovering sorbic acid from its dilute solution.*

* cited by examiner

*Primary Examiner*—Paul J. Killos
*Assistant Examiner*—Mahreen Chaudhry
(74) *Attorney, Agent, or Firm*—Birch, Stewart, Kolasch & Birch, LLP

(57) ABSTRACT

The invented process produces sorbic acid. The process includes the steps of adding a crude sorbic acid to a hot water having a temperature exceeding 100° C., which crude sorbic acid is obtained by the decomposition of a polyester formed through a reaction of ketene with crotonaldehyde, and performing at least one treatment selected from (A) a hot water extraction treatment for extracting sorbic acid with the hot water, and (B) a treatment with an activated carbon in the hot water. The temperature of the hot water is, for example, 120° C. or lower. The amount of sorbic acid to be treated is, for example, equal to or less than the saturated dissolution amount of sorbic acid with respect to the hot water at a treating temperature. The invented process can easily and efficiently remove tar substances and other impurities by-produced in the decomposition of the polyester and can produce a highly purified sorbic acid with a high productivity.

2 Claims, No Drawings

PROCESS FOR THE PREPARATION OF SORBIC ACID

This application is a 571 of PCT/JP99/05126 filed Sep. 21, 1999.

1. Technical Field

The present invention relates to a process for producing sorbic acid which is useful as, for example, food additives. Specifically, the invention relates to a process which is capable of efficiently removing by-produced tar substances and other impurities to produce a highly purified sorbic acid in the production of sorbic acid through the decomposition of a polyester obtained as a polymerized product of crotonaldehyde and ketene.

2. Background Art

Sorbic acid and its salts have antiseptic and antimicrobial activities and are substantially nontoxic to the human body in normal concentrations in use. These compounds are therefore useful as food additives. In a variety of known processes for producing sorbic acid, a commercially important pathway is a process of polymerizing crotonaldehyde and ketene to form an intermediate polyester, and decomposing the polyester to yield sorbic acid. The polyester is decomposed, for example, by thermal decomposition or by hydrolysis in the coexistence of an alkali or acid catalyst. Of these techniques, hydrolysis with a mineral acid, particularly with hydrochloric acid is preferred, as the resulting sorbic acid has a satisfactory yield and quality.

However, according to any of these techniques, by-products are formed during a decomposition reaction and contaminate sorbic acid as impurities and cause coloring of products to thereby deteriorate the quality of products. An extra purification process is therefore required to remove the impurities. This problem also resides in hydrolysis with a mineral acid which is believed to yield relatively satisfactory decomposition results. Specifically, the problem is inevitable even if any other operation condition is added, as far as sorbic acid is prepared by the decomposition of a polyester. Demands have been therefore made to provide a purification process which is capable of efficiently removing by-produced impurities, and various attempts have been made. Generally, a combinationuse of two or more different operations can yield a more highly purified sorbic acid, but most of tar substances having a brown to dark brown color must be removed in a first stage purification operation.

A process is known which includes the steps of decomposing the polyester to yield a wet cake of crude sorbic acid, dissolving the wet cake in a hot water, removing tar portions not dissolved in the hot water by separation, and removing tar portions dissolved in the hot water by treatment with activated carbon. This process requires no special solvent and is advantageous to easily remove large amounts of tar substances. However, the solubility of sorbic acid is at most about 3% even to a hot water around 100° C., and the process requires large-sized facilities to treat large amounts of crude sorbic acid and is disadvantageous in production efficiency.

DISCLOSURE OF INVENTION

Accordingly, an object of the invention is to provide a process which is capable of easily and efficiently removing tar substances and other impurities by-produced in the decomposition of the polyester and is capable of producing a highly purified sorbic acid with a satisfactory productivity.

The present inventors made intensive investigations to achieve the above object and found that tar substances can be efficiently removed by extracting a crude sorbic acid with a hot water at a temperature exceeding 100° C. or treating the crude sorbic acid with activated carbon in a hot water at a temperature exceeding 100° C. This utilizes the fact that the solubility of sorbic acid sharply increases to a hot water having a temperature exceeding 100° C. The present invention has been accomplished based on these findings.

Specifically, the invention provides a process for producing sorbic acid. The process includes the steps of adding a crude sorbic acid to a hot water at a temperature exceeding 100° C., which crude sorbic acid is obtained by the decomposition of a polyester prepared by a reaction of ketene with crotonaldehyde, and performing at least one treatment selected from (A) a hot water extraction treatment for extracting sorbic acid with the hot water, and (B) a treatment with an activated carbon in the hot water. The temperature of the hot water may be, for example, 120° C. or lower. The amount of sorbic acid to be treated may be, for example, equal to or less than the saturated dissolution amount of sorbic acid with respect to the hot water at temperatures to treat the sorbic acid.

BEST MODE FOR CARRYING OUT THE INVENTION

The embodiments of the invention will be described in detail below. According to the invention, a polyester is decomposed to yield sorbic acid. The polyester is obtained by subjecting crotonaldehyde and ketene to a polymerization reaction. Specifically, the polyester is synthetically obtained by blowing ketene into crotonaldehyde in the presence of a catalyst such as zinc acetate, zinc isobutyrate, or α-picoline at temperatures of, for example, about 20° C. to 100° C. Generally, a reaction mixture is distilled to remove excess crotonaldehyde and is then subjected to a decomposition reaction.

The polyester may be decomposed by hydrolysis with an acid or an alkali or by thermal decomposition, but is preferably decomposed by hydrolysis with a mineral acid, particularly with hydrochloric acid, for a higher yield. The polyester is hydrolyzed, for example, at temperatures ranging from about 10° C. to 110° C. When the polyester is hydrolyzed with hydrochloric acid, the concentration of hydrochloric acid is, for example, about 15 to 40% by weight, and preferably about 23 to 36% by weight.

A reaction mixture obtained through the decomposition of the polyester contains tar substances and other impurities by-produced in the reaction, in addition to the sorbic acid and the catalyst used. The production of a high quality sorbic acid therefore requires a purification process.

The invention has a main feature of including the steps of adding sorbic acid obtained through the decomposition of the polyester into a hot water at a temperature exceeding 100° C. and performing at least one treatment selected from (A) a hot water extraction treatment for extracting sorbic acid with the hot water, and (B) a treatment with an activated carbon in the hot water. As the treating temperature is higher than 100° C., these treatments are usually performed under pressure.

In the hot water extraction treatment (A), the crude sorbic acid is sufficiently mixed with the hot water by, for example, stirring, and the resulting mixture is allowed to stand to separate the mixture to an aqueous layer containing sorbic acid and to an organic layer containing by-produced tar substances and other impurities which are not dissolved in the hot water. Thus, sorbic acid can be separated from tar substances and other impurities. In the activated carbon treatment (B), tar substances and other impurities dissolved in the hot water are adsorbed on an activated carbon, and the mixture is filtrated to remove the activated carbon to yield a highly purified sorbic acid.

These treatments (A) and (B) can be performed at any point of time during the purification process of sorbic acid subsequent to the polyester decomposition process. For example, when the polyester is hydrolyzed in the presence of an acid, the reaction mixture is generally a slurry containing sorbic acid dispersed in water, and the reaction mixture slurry is subjected to solid-liquid separation such as suction filtration or filtration under pressure. The resulting crude sorbic acid wet cake is added to a hot water and is then subjected to the above treatments. The crude sorbic acid wet cake contains tar substances and generally has a brown to dark brown color.

In the hot water extraction treatment (A) and/or the activated carbon treatment (B), if the temperature of the hot water is equal to or lower than 100° C., the solubility of sorbic acid is low and thereby the facilities must be large-sized to thereby markedly deteriorate the production efficiency of sorbic acid. If the amount of the crude sorbic acid to be added is increased to avoid the above problem, the sorbic acid is not dissolved in water to induce a large loss in, for example, filtration operation. In addition, tar substances cannot be sufficiently removed by activated carbon and a sorbic acid having a satisfactory hue cannot be significantly obtained.

In contrast, at temperatures exceeding 100° C. (preferably equal to or higher than 103° C., more preferably equal to or higher than 108° C.), the solubility of sorbic acid to water sharply increases, and large amounts of the crude sorbic acid can be treated even in the equal amount of water. Sorbic acid can be therefore produced with a high productivity even in a small-sized production facilities. In addition, tar substances can be effectively removed by activated carbon to thereby yield a high quality sorbic acid having a satisfactory hue.

The melting point of sorbic acid is generally said to be 134.5° C. However, in the coexistence of water, the melting point is supposed to decrease to around temperatures somewhat lower than 120° C., and excess sorbic acid not dissolved in the aqueous layer may liquefy and separate from water at temperatures exceeding 120° C. In the hot water extraction treatment (A), sorbic acid is therefore liable to migrate into the organic layer and to be lost. In the activated carbon treatment (B), the liquefied sorbic acid dissolves tar substances in itself as a solvent to inhibit the activated carbon from removing the tar substances. When such liquefied sorbic acid is cooled, the resulting crystals grab tar substances to cause a deteriorated hue. To efficiently remove tar substances without deteriorating the yield of sorbic acid, the upper limit of the hot water temperature should be preferably set at 120° C., and the amount of sorbic acid to be treated should be preferably equal to or less than the saturated dissolution amount of sorbic acid with respect to the hot water at temperatures to treat the sorbic acid.

Activated carbons for use in the activated carbon treatment (B) include, but are not limited to, activated carbons of plant origin such as wood, sawdust, and coconut shell origin; activated carbons of mineral origin such as peat, brown coal, and lignite origin; and activated carbons of resin origin such as phenol resin origin. The specific surface area of the activated carbon is generally about 200 to 3500m$^2$/g, preferably about 400 to 2000 m$^2$/g, and more preferably about 1000 to 2000 m$^2$/g. The total pore volume of the activated carbon is generally about 0.1 to 2 ml/g, preferably about 0.2 to 1.6 ml/g, and more preferably about 0.8 to 1.6 ml/g.

The amount of the activated carbon can be appropriately selected within a range not deteriorating the purification efficiency and other properties, and is generally about 1 to 20 parts by weight, and preferably about 2 to 15 parts by weight relative to 100 parts by weight of the sorbic acid to be treated with activated carbon.

The treatment with activated carbon is performed for about 10 minutes to 5 hours, preferably about 15 minutes to 2 hours. After the activated carbon treatment, the mixture is filtrated to remove the activated carbon, and the filtrate is cooled to precipitate sorbic acid, and the precipitated sorbic acid is filtrated and dried to give a purified sorbic acid.

Either one or both of the hot water extraction treatment (A) and the activated carbon treatment (B) can be performed.

For example, if the amounts of tar substances are small, the activated carbon treatment (B) alone can yield a sorbic acid having a satisfactory hue. When both the hot water extraction treatment (A) and the activated carbon treatment (B) are performed, a hot water exceeding 100° C. has only to be used in at least one treatment, but should be preferably used in both treatments. The hot water extraction treatment (A) and the activated carbon treatment (B) may be performed stepwise or in one step.

Where necessary, the sorbic acid after the treatment is subjected to a conventional separation and purification means to further improve the hue and purity of the sorbic acid. Such separation and purification means include, for example, crystallization, filtration, centrifugal separation, distillation, and recrystallization.

The present invention will now be illustrated in further detail with reference to an inventive example and a comparative example below. All "parts" are by weight unless otherwise specified.

EXAMPLE 1

To 600 parts of crotonaldehyde, 2 parts of zinc isobutyrate was added as a catalyst, and 170 parts of a ketene gas was introduced at a temperature of 30° C. to 40° C. to perform a reaction. After the completion of reaction, excess crotonaldehyde was removed by distillation under reduced pressure to yield a highly viscous polyester.

To 100 parts of the above-prepared polyester, 380 parts of a concentrated hydrochloric acid was added, and the resulting mixture was heated to 80° C. and was then aged at 75° C. for 60 minutes to decompose the polyester. A reaction mixture was cooled to 25° C. over 1 hour to precipitate a crystalline crude sorbic acid. The crystalline crude sorbic acid was filtrated under reduced pressure and was then rinsed with water to yield a crude sorbic acid wet cake containing 20% by weight of water and 3% by weight of tar substances. To 1500 parts of water in a reactor, 100 parts of the crude sorbic acid wet cake and 3 parts of an activated carbon were added, and the resulting mixture was heated to 110° C. and was held at this temperature for 30 minutes while stirring. The activated carbon and insoluble tar substances were removed by filtration, and the filtrate alone was taken out from the reactor and was cooled to 25° C. to precipitate sorbic acid. The yield of the above-recovered purified sorbic acid with respect to the sorbic acid content in the crude sorbic acid wet cake initially added to water was 91.0%. In 8.8 ml of a 1 N—NaOH aqueous solution, 1 g (on dry basis) of the above-prepared sorbic acid was dissolved to yield a solution. The solution and the aforementioned filtrate each had a light transmittance (color valency) of 79.8% and 91.3%, as determined at a wavelength of 400 nm with a spectrophotometer.

COMPARATIVE EXAMPLE 1

The procedure of Example 1 was repeated, except that the reactor was heated to 100° C. in the activated carbon treatment. The yield of the above-recovered purified sorbic acid with respect to the sorbic acid content in the crude sorbic acid wet cake initially added to water was 60.5%. In 8.8 ml of a 1 N—NaOH aqueous solution, 1 g (on dry basis) of the above-prepared sorbic acid was dissolved to yield a solution. The solution and a filtrate obtained by filtrating off the activated carbon each had a light transmittance (color valency) of 70.1% and 89.8%, as determined at a wavelength of 400 nm with a spectrophotometer.

The invented process performs the hot water extraction treatment and/or the activated carbon treatment by using a hot water having a temperature in a range where the solubility of sorbic acid sharply increases, and can easily and efficiently remove tar substances and other impurities by-produced in the decomposition of the polyester without requiring large-sized facilities. Accordingly, a highly purified sorbic acid having a satisfactory hue can be produced with a high productivity.

What is claimed is:

1. A process for producing sorbic acid, said process comprising the steps of decomposing a polyester, which polyester was formed through a reaction of ketene with crotonaldehyde, to form a crude sorbic acid, adding said crude sorbic acid to water to form a mixture and heating said mixture to a temperature equal to or higher than 108° C., and performing at least one treatment selected from (A) a hot water extraction treatment for extracting sorbic acid with the hot water, and (B) a treatment with an activated carbon in the hot water, wherein the amount of sorbic acid being treated is equal to or less than the saturated dissolution amount of sorbic acid with respect to the hot water at the temperature used to treat the sorbic acid.

2. The process for producing sorbic acid according to claim 1, wherein the temperature of said hot water is 120°C. or lower.

* * * * *